Figure 1:
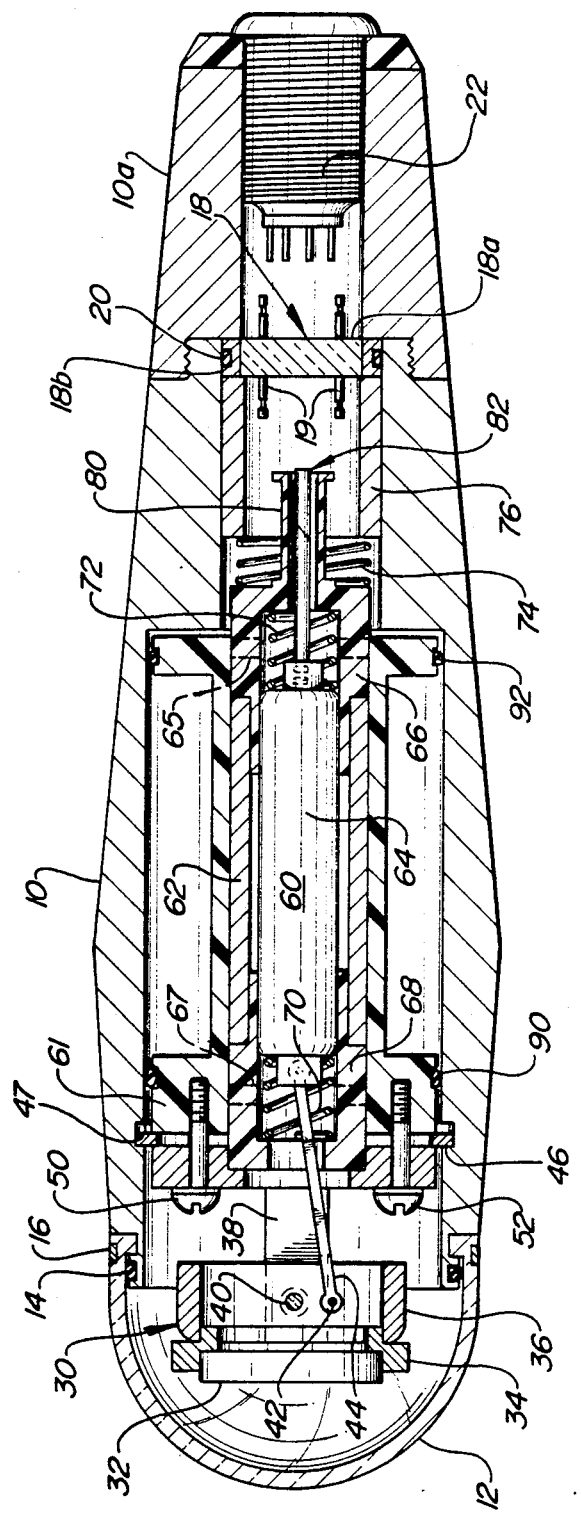

United States Patent [19]

Meyers

[11] Patent Number: 4,688,576
[45] Date of Patent: Aug. 25, 1987

[54] ULTRASONIC TRANSDUCER PROBE ASSEMBLY

[75] Inventor: Paul F. Meyers, San Juan Capistrano, Calif.

[73] Assignee: Technicare Corporation, Solon, Ohio

[21] Appl. No.: 691,319

[22] Filed: Jan. 14, 1985

[51] Int. Cl.[4] ............................................. A61B 10/00
[52] U.S. Cl. ......................................... 128/660; 73/620
[58] Field of Search ................... 248/619, 621; 267/33, 267/136–137, 152; 128/660–661; 73/618–620

[56] References Cited

U.S. PATENT DOCUMENTS

| 4,034,744 | 7/1977 | Goldberg | 128/660 |
| 4,421,118 | 12/1983 | Dow et al. | 128/660 |
| 4,524,623 | 6/1985 | Terwilliger | 128/660 X |

Primary Examiner—Kyle L. Howell
Assistant Examiner—Francis J. Jaworski
Attorney, Agent, or Firm—W. Brinton Yorks, Jr.

[57] ABSTRACT

A mechanical transducer probe assembly is provided which is both rugged and easy to assemble. The probe mechanism is located inside a hollow probe case. A reference point for assembly is located on the inner surface of the case. A motor assembly and a transducer mounting assembly are located within the case and are fixedly joined together. At the jointure of the two, the motor and transducer assemblies are in contact with the reference point, thereby positionally locating the transducer and its drive mechanism within the case. Means are provided for urging the motor and transducer assemblies against the reference point, which means also provides shock mounting for the probe mechanism.

9 Claims, 3 Drawing Figures

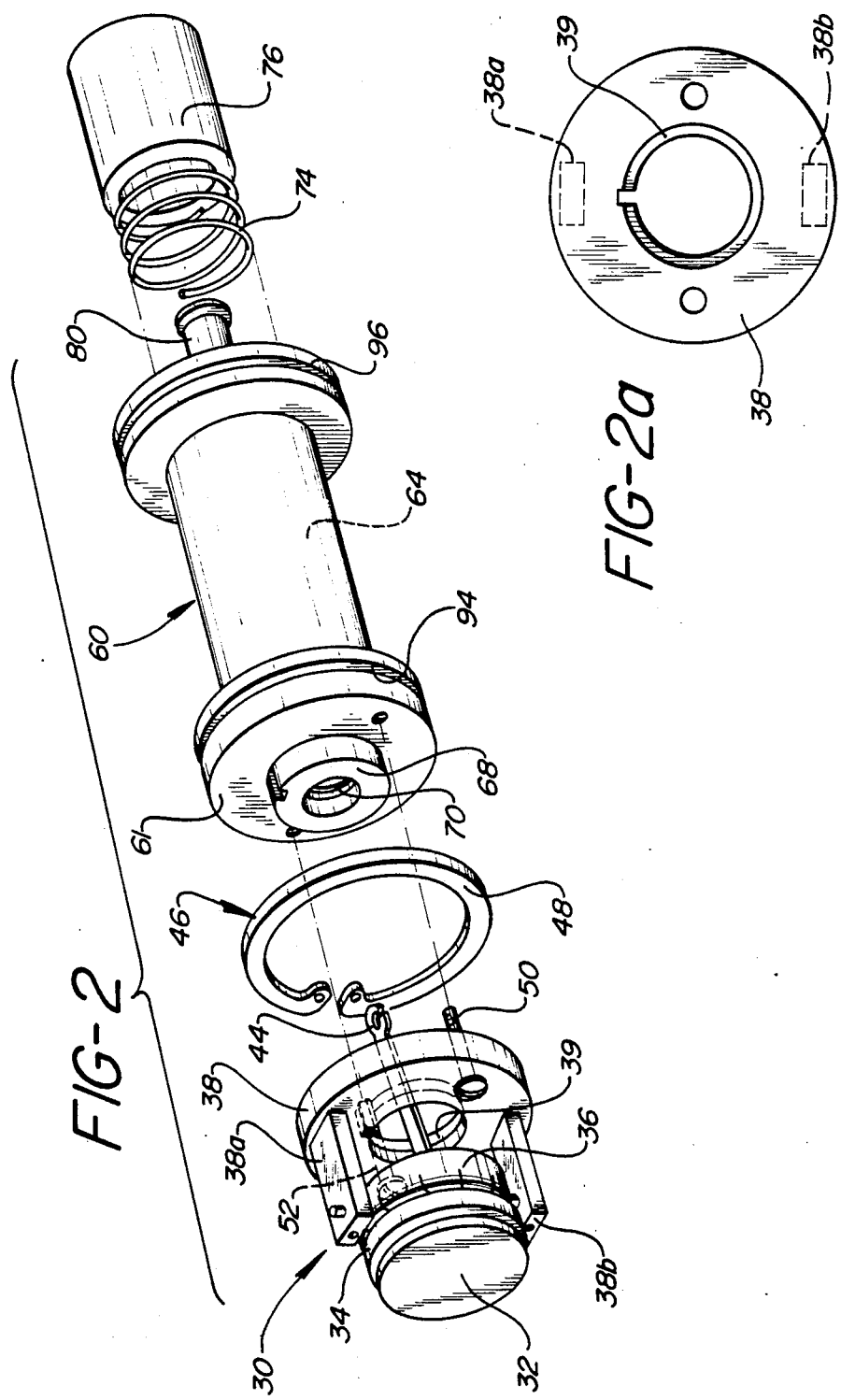

ULTRASONIC TRANSDUCER PROBE ASSEMBLY

This invention relates to ultrasonic transducer probes for use in ultrasonic diagnostic imaging and, in particular, to the assembly of such probes.

Transducer probes for ultrasonic imaging are designed to be small, light, and easy to manipulate for the production of real-time images of the internal tissue structure of a patient. In order to produce real-time images, beams of ultrasonic energy must be rapidly transmitted into the patient and echoes received by the probe for rapid processing in an imaging format suitable for display. Desirably, the probe should produce an image over a wide field of view, such as the so-called sector scan format. A sector scan image is produced by repeatedly transmitting and receiving ultrasonic energy in a number of radial directions from the probe. The ultrasonic beam may be directed either electronically, as by an electronically phased linear array probe, or it may be directed mechanically by a mechanically moving transducer probe. The subject of the present invention is mechanically moving transducer probes, in which the transducer is physically swept through an arc to produce a sector scan. Such mechanical probes may be advantageous compared with phased array probes when a relatively simple mechanical drive assembly in the mechanical probe is used to perform the function of the relatively complex electronics used to "steer" the beam of a phased array probe.

In a mechanical probe, the mechanism used to move, or oscillate, the transducer should be simple and rugged for ease of manufacturability and reliability. The parts of the probe should be capable of being assembled precisely and quickly, without the need for time-consuming, intricate alignment procedures. The finished probe should be capable of withstanding occasional accidental abuse, such as the impact shock of being accidentally dropped.

In accordance with the principles of the present invention, a mechanical transducer probe assembly is provided which is both rugged and easy to assemble. The probe mechanism is located inside a hollow probe case. A reference point for assembly is located on the inner surface of the case. A motor assembly and a transducer mounting assembly are located within the case and are fixedly joined together. At the jointure of the two, the motor and transducer assemblies are in contact with the reference point, thereby positionally locating the transducer and its drive mechanism within the case. Means are provided for urging the motor and transducer assemblies against the reference point, which means also provides shock mounting for the probe mechanism.

In the drawings:

FIG. 1 illustrates a partially cross-sectional view of an ultrasonic transducer probe constructed in accordance with the principles of the present invention; and FIGS. 2 and 2a illustrate in greater detail the transducer and motor assemblies of the probe of FIG. 1.

Referring first to FIG. 1, an ultrasonic transducer probe constructed in accordance with the principles of the present invention is shown. The probe elements are housed in a case 10, which may be machined from aluminum, or molded delrin, polysulfone or similar material. An acoustic cone or cap 12 is fitted at the end of the case. The cap 12 is made of polyethylene or other material which is highly transmissive to ultrasound. During use, ultrasonic energy passes through the cap 12 to and from an ultrasonic transducer 32 by way of the intervening fluid inside the probe. The acoustic cap 12 is fitted into a groove around the periphery of the open end of the case, and is sealed by a plastic compression band 16. This seal is made fluid-tight by an O-ring 14 compressed between the cap 12 and the case 10.

A transducer mounting assembly 30 includes illustrated components 32 through 38. The transducer 32 is seated in a transducer ring 34. The transducer ring 34 then snaps into place in a transducer cup 36. This permits the manufacture of a variety of transducers of different characteristics in transducer rings of the same outer dimension. When a customer orders a probe with a specified transducer, the selected transducer and ring module can be snapped into the transducer cup with the necessary electrical connections being made.

The transducer cup 36 contains ball bearing fittings on either side, with a hard steel axle pin 40 passing therethrough. A stainless steel crank pin 42 is press fit through the transducer cup parallel to the axle pin 40. In a constructed embodiment of the present invention, the crank pin 42 is spaced apart from the axle pin 40 by a distance of 0.090 inches. This exemplary spacing is one of the determining factors of the angle through which the transducer is oscillated. In the constructed embodiment, the oscillation angle was 90 degrees. It was found that a one thousandth of an inch variation in the spacing distance corresponded to approximately a one degree variation in the oscillation angle.

One end of a crank shaft 44 is connected to the crank pin 42 in a bearing fit. The other end of the crank shaft 44 is connected to the moving magnet assembly 64 of the motor assembly 60, also in a bearing fit. The ends of the axle pin 40 which extend from the transducer cup 36 are located in holes in the arms which extend from the base of a gimbal cup 38. The axle pin is held firmly in the holes in the gimbal cup arms by orthogonally directed set screws in the gimbal cup arms. The gimbal cup is held in place in the probe by screws 50 and 52, which pass through holes in the gimbal cup base and into threaded holes in an expansion bushing 61, which surrounds the motor. The base of the gimbal cup and the spool-shaped expansion bushing thereby sandwich a snap ring 46, which extends around a groove 47 in the inner circumference of the case 10.

A motor assembly 60 includes components numbered 61 through 68. An upper bearing 68 of the motor is fitted at one end into an annular groove in the base of the gimbal cup 38. A lower bearing 66 is held in place by a shock mounting spring 74 and a tube 76, the latter contacting a glass/metal seal 18. The inner portion 18a of the seal is made of glass, and has a number of electrical connection pins 19 passing through it. Leads from the transducer, the motor and the position sensor (not shown) are connected to these pins. The outer periphery 18b of the seal is made of metal, and is surrounded by an O-ring 20. This O-ring 20 forms a fluid tight seal at the back of the probe, and terminates the fluid compartment in which the motor and transducer assemblies are located. Connections are then made between the connection pins on the outside of the fluid compartment and a connector 22. The connector 22 may be mated with a corresponding plug on the end of a cable, thereby bringing the necessary signals to and from the probe.

The crank shaft 44 passes through holes in the base of the gimbal cup 42 and the upper bearing 68, and is connected to the magnet assembly 64. The magnet assembly slides in a reciprocating manner in the bearings 68 and 66, which are made of delrin. Compression springs 70 and 72 are located at either end of the magnet assembly, and serve to locate the magnet assembly in a central position of the motor when the motor is not operating. In this position, the transducer is located facing directly ahead, as shown in the drawing. The compression springs 70, 72 also assist the motor at turn-around, the times at which the magnet assembly 64 is reversing its direction of travel. The cylindrical magnet assembly 64 is surrounded by a tubular coil assembly 62. A position sensor pin 82 is screwed into a threaded hole at the lower (right hand) end of the magnet assembly. As the coil assembly 62 is energized, the magnet assembly 64 moves back and forth, or horizontally in the drawing. The crank shaft 44 is thereby reciprocated back and forth, which moves the transducer cup and transducer in oscillatory fashion about the axle pin 40. At the same time, the magnet assembly moves the position sensor pin 82 through a position sensor coil form 80, which is formed as a part of the lower bearing 66. A coil (not shown) is wound around the coil form 80, and the movement of the position sensor pin 82 through the coil changes the inductance of the coil in relation to the location of the pin and correspondingly the angular orientation of the transducer. This changing inductance is sensed and used to establish the instantaneous position of the transducer.

A detailed description of the construction and operation of the motor and position sensor may be found in concurrently filed U.S. patent application Ser. No. 691,320 filed Jan. 14, 1985 entitled "ULTRASONIC TRANSDUCER PROBE DRIVE MECHANISM WITH POSITION SENSOR."

Referring now also to FIGS. 2 and 2a, the transducer mounting assembly 30 and the motor assembly 60 of FIG. 1 are shown with their associated assembly components. The transducer 32 is seated in the transducer ring 34 and sits on a layer of a resilient, soft rubber material. The rubber material acts to substantially acoustically isolate the transducer from the transducer ring and the mounting assembly, thereby largely preventing the coupling of ultrasonic vibrations into the assembly. This prevents the generation of reverberation and corresponding image artifacts in the probe and its imaging system.

The transducer and ring are shown snapped into the transducer cup 36, which in turn is pivotally mounted between arms 38a and 38b of the gimbal cup 38. At the ends of the arms 38a and 38b can be seen the set screws which hold the axle pin securely in the gimbal cup. The crank shaft 44 is connected to the crank pin behind the transducer and extends through the hole in the base of the gimbal cup 38.

To the right of the transducer mounting assembly 30 is a bushing clip or snap ring 46. Behind the snap ring is the motor assembly 60. Within the smaller diameter central portion of the expansion bushing 61 are the magnet assembly 64 and the coil assembly 62, which are not visible in this drawing Figure. Extending from the opening at the forward end of the expansion bushing is the upper bearing 68. When the probe is assembled the upper bearing is seated in the annular groove 39 around the hole at the back of the base of the gimbal cup 38. The groove 39 is shown in the plan view of the back of the gimbal cup in FIG. 2a. Grooves 94 and 96 in the larger diameter ends of the expansion bushing 61 accommodate O-rings 90 and 92 (FIG. 1), which form fluid-tight seals between the ends of the expansion bushing and the inner surface of the case 10. The position sensor coil form 80 is shown extending from the back of the motor assembly.

Behind the motor assembly 60 are the shock mounting spring 74 and the tube 76.

Assembly of the probe proceeds as follows. First, the glass/metal seal 18 with its O-ring 20 is seated at the back of the probe. The tube 76 and the shock mounting spring 74 are then slipped into the case, with the tube 76 contacting the seal 18. The motor assembly 60 then slides into the case, with the lower bearing 66 in contact with the shock mounting spring 74. With the shock mounting spring 74 in its uncompressed state, the motor components inside the expansion bushing 61, including the magnet and coil assemblies 64 and 62 and the upper and lower bearings 68 and 66, will be pushed forward by the spring 74 and out the front end of the bushing 61. The expansion bushing 61 encounters only the resistance of the O-rings 90 and 92 in contact with the inner walls of the case 10, and may be pressed to its final position as shown in FIG. 1. The motor components fit loosely inside the expansion bushing 61 so that there is a cavity for fluid surrounding the coil assembly and bearings 66 and 68. This fluid cavity retains the fluid pumped in and out of the holes 65 and 67 in the bearings 66 and 68 as the motor operates.

Next, needle-nosed pliers are used to compress the snap ring 46 to a smaller diameter for insertion into the case. The snap ring is aligned with the groove 47 around the inner circumference of the case and the pliers are released so that the snap ring snaps into place in the groove 47. The dimensions of the groove are not critical, and the snap ring may fit loosely in the groove at this time. Only the location of the forward edge of the groove is important, as the final assembly step will show.

Lastly, the transducer mounting assembly is inserted into the probe. The crank shaft 44 is hooked or snapped onto a pin at the end of the magnet assembly 64 as shown in FIG. 1. The annular groove 39 is fitted around the end of the upper bearing 68, which extends out the end of the expansion bushing 61. The transducer mounting assembly is now securely located by tightening screws 50 and 52, which thread into holes in the expansion bushing 61. As the screws are tightened the force of the shock mounting spring 74 is encountered as the base of the gimbal cup 38 pushes the motor components toward the back of the probe. When the screws are fully tightened the shock mounting spring 74 is in its compressed state.

The probe components are now securely and accurately located in the case through a combination of forces interacting through the probe components. The force of the compressed shock mounting spring is directed to the front and back of the probe. The force toward the back is directed through the cylinder 76 to the glass/metal seal 18, which holds the seal firmly in place. This helps to maintain the integrity of the fluid seal formed by O-ring 20. The forward-directed spring force urges the lower bearing 66, the coil assembly 62, and the upper bearing 68 of the motor securely against the base of the gimbal cup 38, which holds the motor components in place. This forward spring force is then directed back to the expansion bushing 61 through the screws 50 and 52, which pull the expansion bushing forward and sandwich the snap ring 46 between the gimbal cup 38 and the expansion bushing 61. The sandwiched snap ring 46 is ultimately pressed forward by the force of the shock mounting spring 74, thereby positioning the snap ring with its front face 48 pressed firmly against the front edge of the groove 47. In this way, the transducer mounting assembly 30 and the motor assembly 60 are positionally located in the case 10 with reference to this front edge of the groove 47.

In addition to these functions of pressing the glass/metal seal in place and positionally locating the probe components, the spring 74 also provides shock mounting protection for the probe components. If the probe is accidentally dropped and lands on its end at the connector 22, the spring 74 will compress upon impact and absorb much of the force of the fall. The motor components will be thrown toward the connector 22, but this force will be cushioned by the shock mounting spring 74. It is desirable for the spring 74 to exhibit a selected amount of compression, being neither too loosely nor too greatly compressed. The former will allow the motor components to wobble or oscillate during operation, and the latter will reduce the cushioning ability of the shock mounting spring. The degree to which the spring is compressed is chosen by selecting a length for the tube 76 which is appropriate to compress the spring 74 by the desired amount. The degree to which the spring 74 is compressed may thus be a matter of design choice, depending upon the characteristics of the particular spring being used.

The transducer probe of FIG. 1 is also capable of withstanding impact shocks applied in other directions. If the probe is dropped on its front end, the soft plastic cap 12 will compress to absorb most impact forces. A severe fall onto a hard surface may crack the cap 12. This will require replacement of the cap and fluid, but will usually not require repair of the transducer mounting assembly and the motor assembly. Impacts on the side of the probe may be absorbed through the use of a plastic case. In addition, the O-rings 90 and 92 and the fluid cavity surrounding the bearings 66 and 68 and the coil assembly 62 will provide some degree of cushioning of the motor components. The fluid within the probe will also help to damp the forces of falls in virtually every orientation.

In a constructed embodiment of the present invention, it has been found desirable to fabricate the case 10 in two pieces for several reasons. As shown in FIG. 1, the rear portion 10a of the case, which holds the connector 22, is a separate part which is threaded to screw onto the main part of the case 10. With case part 10a removed assembly ease is further afforded since it is no longer necessary to slide the seal 18 all the way down from the front of the case. This can be difficult, because the O-ring 20 can bind as the seal is pushed through the narrow portion of the case. In the preferred configuration, the seal is fitted in from the rear with part 10a removed, thereby obviating any binding problem. Furthermore, different parts 10a can be fabricated with different sizes and styles of connector. During final assembly, a part 10a with the connector desired by the user can be selected, wiring connections made, and the part screwed into place.

Variations consistent with the principles of the present invention may also be employed. For instance, instead of using a groove to locate the snap ring, an annular projection or a series of individual projections around the inner circumference of the case may be formed to locate the snap ring. The snap ring would then press against a planar side of these projections. The projections would have to be dimensioned so as to permit passage of the expansion bushing with its O-rings by them when inserting the motor assembly 60 into the case. While this may present serious assembly problems in a one-piece case, it may be a desirable alternative when a two-piece, clamshell-like case is used. The motor assembly and the rear spring, tube and seal could then be located in the probe before the two-piece case is closed and sealed. In such an arrangement, the snap ring could be replaced by an annular ridge extending out from the inner circumference of the case, located in the location of the groove 47 and sandwiched by the transducer mounting assembly and the compression bushing. However, the accurate dimensioning of both the front and back faces of the ridge would be necessary, since the ridge would be immobile in the case. Additionally, this alternative would be more desirable in a metal case than a plastic case, since a plastic ridge may not provide the requisite structural strength. In a plastic case, the groove and snap ring arrangement of the preferred embodiment is more desirable for structural integrity.

What is claimed is:

1. An ultrasonic transducer probe, in which a drive mechanism is used to oscillate an ultrasonic transducer, comprising:
   a hollow probe case for containing elements of said probe, including an annular projection located on the inner surface thereof and marking the intended terminuses of a forwardly located transducer assembly and a rearwardly located motor assembly;
   a motor assembly, located in said case, and having a forward end;
   a transducer assembly, located in said case and including means, having a rearward end, for mounting said ultrasonic transducer for oscillation; and
   means for fixedly positioning said motor assembly and said transducer assembly within said case by connecting them together so that said forward end of said motor assembly and said rearward end of said transducer mounting means securely sandwich said annular projection,
   wherein a moving element of said motor assembly is connected to said transducer assembly by a connecting element passing through said sandwich connection.

2. The ultrasonic transducer probe of claim 1, further comprising means for urging said motor assembly and transducer assembly in fixed relationship with the location of said annular projection on the inner surface of said case.

3. The ultrasonic transducer probe of claim 1 wherein said annular projection includes a snap ring, located in said probe case in contact with an annular groove within said case, wherein said snap ring is sandwiched by said forward and rearward ends.

4. The ultrasonic transducer of claim 3, wherein said sandwich connection includes screws.

5. The ultrasonic transducer probe of claim 1, wherein said mounting means includes a gimbal cup for pivotally mounting said transducer.

6. The ultrasonic transducer probe of claim 5, wherein said transducer assembly includes a ring for holding said transducer, said ring and transducer being snap-fit into said gimbal cup.

7. An ultrasonic transducer probe, in which a drive mechanism is used to oscillate an ultrasonic transducer, comprising:

a hollow probe case, including a reference indicator on the inner surface thereof, for containing elements of said probe;

a motor assembly, located in said case, and having a forward end;

a transducer assembly, located in said case and including means for mounting said ultrasonic transducer for oscillation, and having a rearward end; and means for connecting said motor assembly to said transducer assembly at a jointure of said forward and rearward ends, said jointure being fixedly positioned by said connecting means in reference to said reference indicator;

further comprising means for urging said motor assembly and transducer assembly in fixed relationship with said reference indicator, wherein said motor further has a rearward end, and said urging means including a spring located at said rearward end of said motor for urging said forward end of said motor in fixed relationship with said reference indicator.

8. The ultrasonic transducer probe of claim 7, wherein said reference indicator includes a groove in the inner surface of said hollow case, and wherein said connecting means includes a snap ring located in said groove.

9. The ultrasonic transducer probe of claim 8, further including a spacer located between said rearward end of said motor and an inner surface of said probe for effecting a desired compression of said spring.

* * * * *